Figure 3:
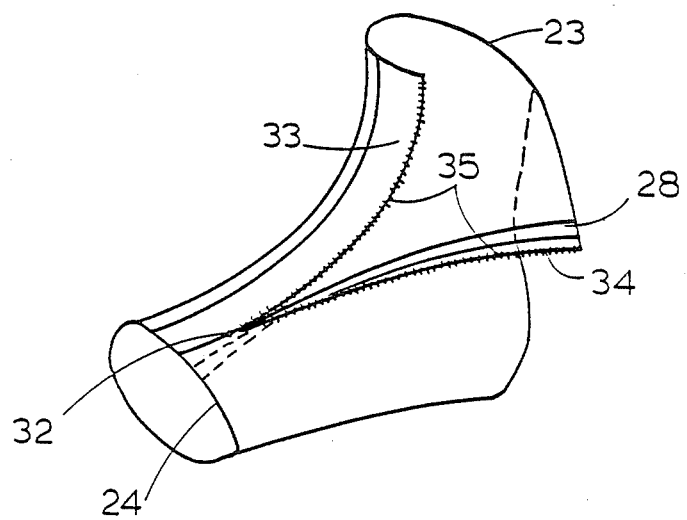

United States Patent [19]

Huntjens

[11] Patent Number: 4,702,234
[45] Date of Patent: Oct. 27, 1987

[54] SUPPORT FOR AIDING PROPRIOCEPTIVE INNERVATION

[75] Inventor: Jozef H. G. Huntjens, Schinnen, Netherlands

[73] Assignee: MacIntosh N.V., Stein, Netherlands

[21] Appl. No.: 903,491

[22] Filed: Sep. 4, 1986

[30] Foreign Application Priority Data

Sep. 17, 1985 [NL] Netherlands .................. 8502536

[51] Int. Cl.⁴ .................. A61F 3/00; A61F 13/06; A61F 13/10
[52] U.S. Cl. .................. 128/77; 128/80 H; 128/165; 128/166
[58] Field of Search .................. 128/80 R, 80 H, 156, 128/165, 166, 166.5, 77

[56] References Cited

U.S. PATENT DOCUMENTS

| | | | |
|---|---|---|---|
| 999,010 | 7/1911 | Collis | 128/166 |
| 1,462,534 | 6/1921 | Condylis et al. | 128/165 |
| 2,994,322 | 8/1961 | Cullen et al. | 128/80 H |
| 3,533,407 | 10/1970 | Smith | 128/165 |
| 3,595,244 | 7/1971 | Kugler | 128/582 |
| 3,934,583 | 1/1976 | Hollingshead et al. | 128/165 |
| 4,084,586 | 4/1978 | Hettick | 128/80 H X |
| 4,166,460 | 9/1979 | Applegate | 128/80 H |
| 4,309,991 | 1/1982 | De Marco | 128/165 |
| 4,323,058 | 4/1982 | Detty | 128/80 H |
| 4,479,495 | 10/1984 | Isaacson | 128/327 |
| 4,550,721 | 11/1985 | Michel | 128/80 E |
| 4,556,054 | 12/1985 | Paulseth | 128/80 H |
| 4,625,336 | 12/1986 | Derderian | 2/79 |

FOREIGN PATENT DOCUMENTS 529151 7/1931 Fed. Rep. of Germany .

Primary Examiner—Clifford D. Crowder
Attorney, Agent, or Firm—Cushman, Darby & Cushman

[57] ABSTRACT

The inner surface of a support for a part of the body, particularly for a joint, is provided with a part having an increased coefficient of friction in respect of the skin compared with the rest of the inner surface, the part with the increased coefficient of friction being situated at that place that is in contact, after the application of the support, with parts of the surface of the skin having muscular and/or tendinous tissue underneath which tissue can be innervated proprioceptively to initiate one particular change in position between skeleton parts situated on either side of the joint.

11 Claims, 9 Drawing Figures

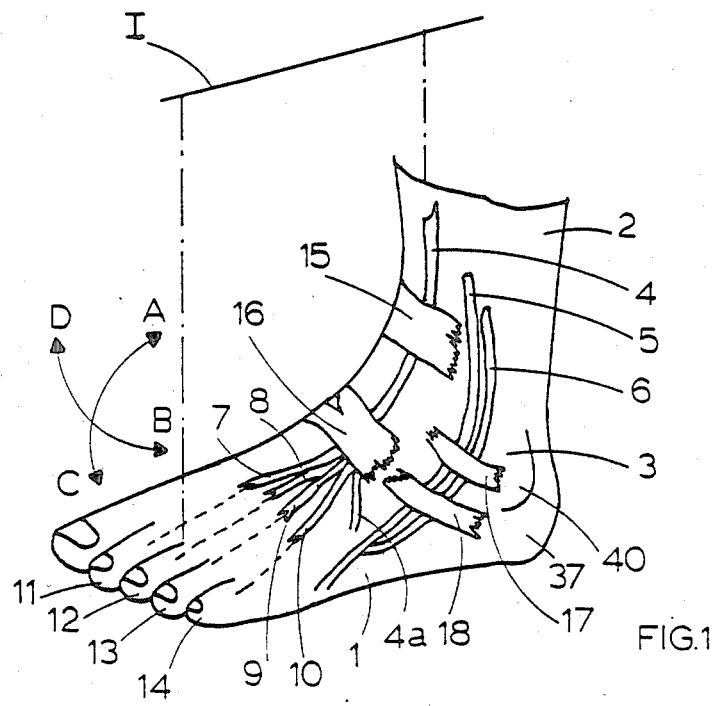
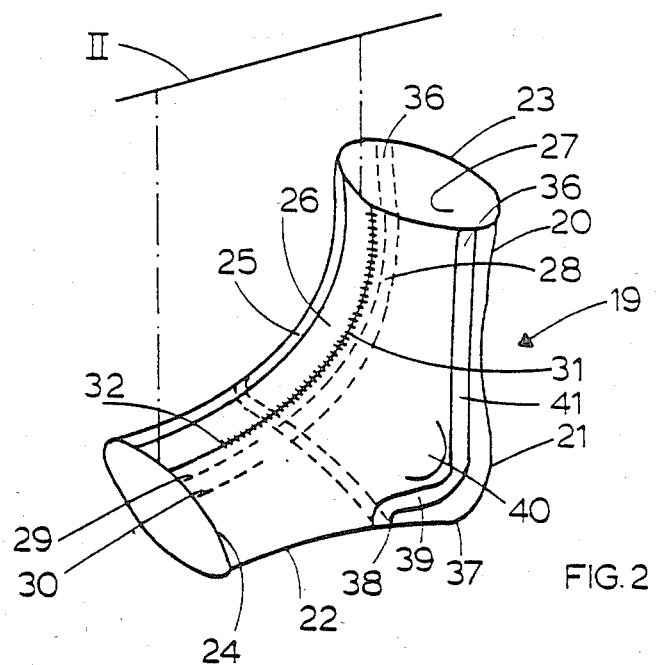

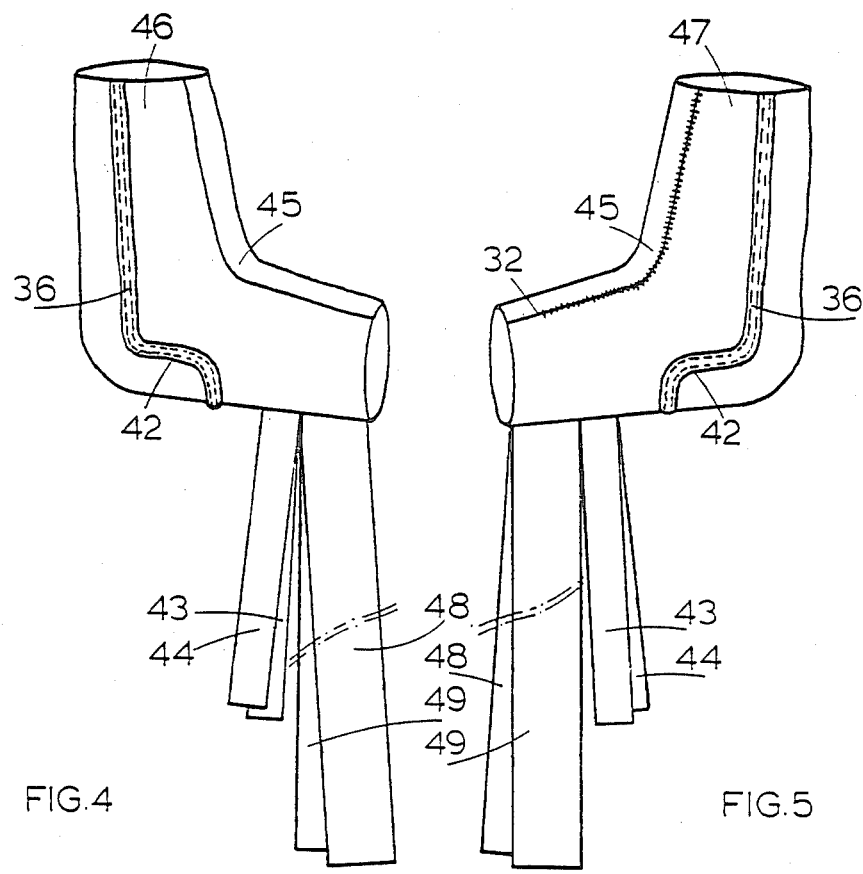

SUPPORT FOR AIDING PROPRIOCEPTIVE INNERVATIONg

The invention relates to a support for a part of the body, particularly for a joint, comprising a sleeve or wrapper made substantially from elastic material and extending, after its application, between a proximal line and a distal line in respect of the joint, to which sleeve or wrapper optionally a bandage is fastened to provide greater pressure on and/or more support to the part of the body.

Such supports are known as ankle supports from U.S. Pat. No. 1,027,897 and U.S. Pat. No. 3,084,023 and as wrist supports from U.S. Pat. No. 3,710,790 and U.S. Pat. No. 3,238,939. These supports have the property of providing, after their application round the part of the body for which they are intended, within certain limits, through the sleeve or wrapper or additionally with their bandages, an exclusively mechanical immobilization of the parts of the skeleton on either side of a joint.

The invention provides a support which has the additional advantage of the body itself being stimulated to contribute to the supporting effort.

This is achieved in that on the inner surface of the support the surface is provided with a part having an increased coefficient of friction in respect of the skin compared with the rest of the inner surface, and in that that part of the surface is situated at that place that is in contact, after the application of the support, with parts of the surface of the skin having muscular and/or tendinous tissue underneath which tissue can be innervated proprioceptively to initiate one particular change in position between skeleton parts situated on either side of the joint.

Proprioceptive innervation of the musculature is understood to mean in this connection the increase in the muscular tension by proprioceptively sensible receptors present in the muscular or tendinous tissue passing stimuli on to the central nervous system, which in its turn influences the muscular action. The proprioceptive sensibility must be distinguished from the exteroceptive sensibility with the stimuli from the environment being transferred to the central nervous system via the organs of sense. With the proprioceptive sensibility stimuli from the body itself are further conveyed to the central nervous system.

The invention utilizes the presence of proprioceptive sensibility. Care is taken that particular parts of the skin having, underneath, receptors to be stimulated should be covered with material having a very low slipping effect on the skin, sticking to the skin as it were. When the parts round the joint are moved, the skin is moved to and fro and massages the deeper tissue in which the receptors are contained. As a result, the muscle in which the receptors are contained is contracted and a higher tension is brought about in the muscle and tendon so that a change in position can be initiated between two skeleton parts situated on either side of a joint. The nonslipping parts of the surface are so placed as to initiate exactly that change in position that will relieve a damaged or weak ligament.

Indeed, from German Pat. No. 3,225,088 and British Pat. No. 2,077,565 supports are known parts of the inner surfaces of which have an increased coefficient of friction in respect of the skin. These non-slipping parts of the surface are, however, only intended to keep the support at its place and do not serve any muscular innervation purposes.

In the specification following hereinafter the Latin nomenclature will be used to indicate the parts of the body if such is necessary for reasons of clarity, with the English names in brackets behind, if possible, Moreover, in the specification below the following is understood by distal: away from the trunk;
proximal: towards the trunk;
medial: on the inside of the part of the body;
lateral: on the outside of the part of the body;
radial: on the side of the forearm or hand where the radius (spoke bone) is situated;
ulnar: on the side of the forearm or hand where the ulna is situated;
palmar: on the inside of the hand or wrist.
plantar: on the side of the sole of the foot;
dorsal: on the side of the back of the hand or wrist or on the upper side of the foot;
sagittal plane: a plane parallel to a vertical plane dividing a standing human body accurately into a left-hand side and a right-hand side.

These designations are used also in describing supports that are considered as having been applied round the relative part of the body.

The parts of the surface having an increased coefficient of friction in respect of the skin are preferably formed from pieces of natural chamois leather stuck or sown to the inside of the sleeve or wrapper. The fact is that the property of natural chamois is that already in dry condition it has a coefficient of friction in respect of the skin which is higher than that of the customary textile materials used for supports. When it becomes damp and wet, chamois leather shows even a much higher coefficient of friction, which is an advantage for the object of the invention, because the moisture content of the inside of a support applied to the skin will increase rapidly as a result of perspiration.

The part of the surface having an increased coefficient of friction may be discontinuous. This is an advantage when the part of the surface having an increased coefficient of friction consists of material less elastic than the material of the rest of the support.

The part of the surface with an increased coefficient of friction in respect of the skin belonging to an ankle support serving an area between proximal and distal in respect of the tarsus may be situated in a strip of the support between the proximal and distal limits, which strip will be in contact, after the application of the support, with a strip of the skin situated in a lateral position in respect of a sagittal plane between the second and the third toe. The advantage of such a support is that it is suited for the vast majority of ankle injuries. The fact is that the most frequent ankle injury is the spraining or rupture of the ligamentum talofibulare anterius, a ligamentum (a ligament) connecting the talus (ankle bone) with the fibula (calf bone) and respectively fastened to the collum tali and the malleolus lateralis (external malleolus). The said injury is usually caused by spraining in consequence of which an excessive inward bending of the foot occurs, whether or not in combination with a plantar flexion. The muscular and tendinous system capable of opposing the said bending is formed by a. the m. tibialis anterior (anterior shinbone muscle), b. the m. extensor hallucis longus (long extensor for the big toe), c. the m. extensor digitorum longus (long toe extensor), d. possibly the m. peronaeus tertius, e. the m. peronaeus longus (long calfbone mucle) and f. the m. peronaeus brevis (short calfbone muscle). The abreviation m. stands for musculum (muscle). Said muscles proceed as tendons in the said order a. up to and including f., from medial to lateral, side by side, from the leg below the knee, over the front and lateral side of the area between the leg below the knee and the foot, down into the foot. They are situated in a separate or in a common vagina synovialis (sheath of a tendon) fixed sideways under the retinaculum extending crosswise in respect of the leg below the knee and the foot.

When the foot is moved, the part of the surface with an increased coefficient of friction in the ankle support according to the invention takes the skin along, which passes this movement on via the retinaculum and possibly even other thin layers of tissue to the underlying tendons c. up to and including f. in which the proprioceptively sensible receptors are situated.

An ankle support particularly suited for applying the invention is characterized in that the support consisting of a first elastic material substantially consists of a sleeve which is bent in the shape of a foot and open at both ends, comprising a straight leg portion terminating in an edge of the leg portion, a bent heel portion linking up with the leg portion and a straight foot portion linking up with the heel portion and terminating in an edge of the foot portion, in that on the concave side of the sleeve a strip of the support extending between the edge of the leg portion and the edge of the foot portion consists of a second elastic material having a greater elasticity than the first elastic material and in that on the concave side, between the first and the second elastic material, a split has been provided from the edge of the leg portion to near the edge of the foot portion, which split can be closed with fasteners. This support with split has a wide instep and precludes any extra difficulties in the application of the support, usually already a close fit round the part of the body as it is, arising on account of the greater friction of the inner surface on the skin. As the split does not extend quite up to the edge of the leg portion, the support can be positioned more easily before closing the split. This is particularly an advantage in the positioning of any existing parts of the surface with an increased coefficient of friction. The strip with the second elastic material may overlap a few sizes, which depresses the manufacturing costs.

The action of the ankle support described above, which is based on the proprioceptive sensibility, can even be further improved by providing the support with two cross bandages fastened before the heel portion, to the sole of the foot portion of the support, both of them having a length sufficient for the one, the medial cross bandage, to be fastened medially along the foot portion, crosswise over the instep and laterally on the proximal side of the support and for the other, the lateral cross bandage, to be fastened laterally along the foot portion, crosswise over the instep and medially on the proximal side of the support. At those places where they cross the underlying parts of the surface that have an increased coefficient of friction, the cross bandages then exercise an additional pressure on these parts and the medial cross bandage will pull the foot into the desired direction, while the lateral cross bandage precludes too great an abduction of the foot resulting from the joint effect of the pull of the medial cross bandage and the pull of the proprioceptively innervated muscles.

The cross bandages described above are also an advantage on ankle supports that make no use of the proprioceptive sensibility, so on sleeves or wrappers the surfaces of which have no parts with an increased coefficient of friction in respect of the skin. The fact is that these short cross bandages fix the foot within certain limits of deviation thereby protecting ligaments against overloading.

Using one or more further long bandages fastened to the sleeve or wrapper, the whole of it can be covered while pressure is being applied at those places where such is necessary in connection with, for instance, a hemorrhage under the skin.

It is to be recommended to make the (short) cross bandages from a material the elasticity of which is lower than that of the long bandages. As a result, these bandages will serve their purpose better, viz. to cope with pulling forces.

The separate functions of the short cross bandages and the long bandage(s) involve a more direct action of the support.

The proprioceptive action of the ankle support described can even be further improved by fastening to the support a busk passing before the heel under the foot, coming up along the medial and lateral sides of the foot and bending backwards to beyond the areas where the malleolus medialis and the malleolus lateralis are to be found after the application of the support, the busk extending from here vertically behind the malleoli as far as the edge of the leg portion of the support. A support provided with such a busk will try to pull the part of the inner surface before the busk, which part has an increased coefficient of friction in respect of the skin, from its place already in a light plantar flexion of the foot, so that the skin, too, will be taken along, and consequently the underlying muscular and/or tendinous tissue will be better massaged to stimulate the proprioceptively sensible receptors.

Even without reaching a proprioceptive action, this busk offers the advantage that it is not an impediment while walking and standing, that it opposes the rotation of the foot round the longitudinal axis of the foot and that it maintains the bent shape of the support. The busk can be incorporated in stitchings applied on the outside of the support.

With a wrist support serving an area between proximal and distal in respect of the carpus (wrist joint), the part of surface having an increased coefficient of friction in respect of the skin may be situated in an area extending from the proximal side of the support, which area is in contact, after the application of the support, with the palmar and ulnar parts of the skin of the forearm and the hand. The advantage of such an elastic bandage is that it is suited for the vast majority of the injuries of the articulationes carpi (carpal joints). The fact is that most of the wrist injuries are due to excessive dorsal flexions of the hand, resulting in excessive stretching of one or more ligaments on the palmar side of the carpus between each of the eight carpal bones or between the carpal bones and the bones of the forearm, so the radius (spoke bone) and/or ulna. The muscular and/or tendinous tissue nearest to the surface on the ulnar and palmar sides of the forearm and hand, which oppose a dorsal flexion and may therefore relieve the damaged ligaments is the muscular tissue of a. the m. flexor carpi ulnaris, b. the m. flexor digitorum superficilis, c. the m. palmaris longus and d. the m flexor carpi radialis. In the said order a–d, from the ulnar sides of the forearm and hand to the radial sides of the forearm and hand, these muscles extend side by side as tendons from the forearm onwards into the hand. The m. flexor carpi ulnaris is fastened to the os pisiforme (pisiform bone), extending further to the os hamatum (hamate bone), to the metacarpal bone of the little finger. The m. flexor digitorum superficialis is fastened with four tendons, each of them splitting up into two sub-tendons, to the edges on both sides of the middle phalanges of the 2nd up to and including the 5th finger. The m. palmaris longus spreads out into the palmar flat of the hand up to the proximal phalanges of the 2nd up to and including the 5th finger. The m. flexor carpi radialis is fastened to the metacarpal bone of the 2nd, sometimes also of the 3rd finger. The m. flexor carpi ulnaris and the m. palmaris longus excepted, all the said muscles and their tendons pass through the canalis carpi, these are ducts between the retinaculum covering the tendons and carpal bones. Here the tendons are separately or jointly enveloped by a vagina synovialis when the skin is moved to and fro, the muscular and tendinous tissue described above is proprioceptively innervated by the wrist support to initiate a palmar flexion relieving the weak or damaged ligaments.

A wrist support according to the invention which is excellently suited to do justice to the proprioceptive action and which is, moreover, suited for injuries of the joint of a thumb is characterized in that the support is a substantially rectangular wrapper with a distal side of the rectangle and a proximal side of the rectangle parallel to it, a palmar side of the rectangle and a dorsal side of the rectangle parallel to it, which wrapper can be shaped to form a sleeve by means of fasteners along the palmar and dorsal sides of the rectangle, in that there is a U-shaped recess between the palmar and dorsal sides of the rectangle having its mouth on the distal side of the rectangle, which recess is bridged, between the legs of the U, by two elastic strips of material having a greater elasticity than the material of the wrapper, the first of which extends from the ends of the legs of the U and the second from the closed end of the U in such a manner that a thumb can be inserted between the bridging strips, in that an elastic bandage is present fastened to the dorsal side of the rectangle and having sufficient length to cover the way: palmar, radial, dorsal sides of the forearm, ulnar and palmar sides of the hand, between thumb and forefinger obliquely over the dorsal side of the hand, over ulnar, palmar and radial sides of the forearm and then obliquely to the dorsal side of the hand, and in that the bandage is provided on its proximal side with a recess for the portion applied between thumb and forefinger.

The strip extending from the closed end of the U may have an excess of material for the bridging function. Thus a good fit round the base of the thumb can be achieved with sufficient support for the thumb.

The invention will be further elucidated hereinafter with reference to a few typical embodiments forming part of the invention and represented in the drawing.

The drawing shows in

Figure 6:
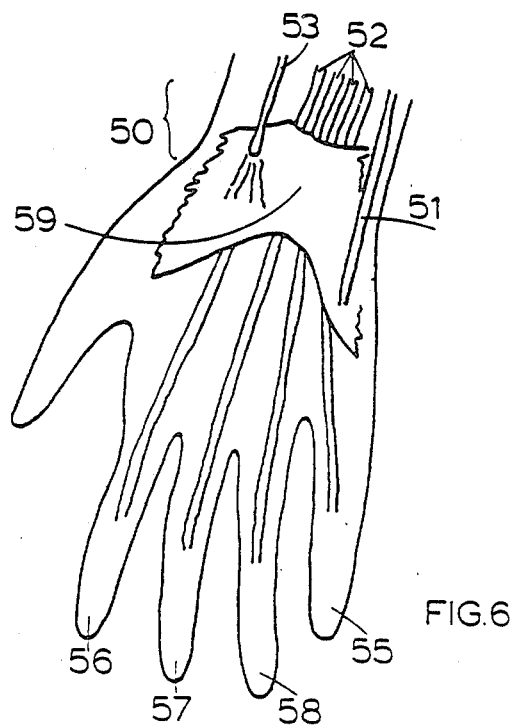
Figure 7:
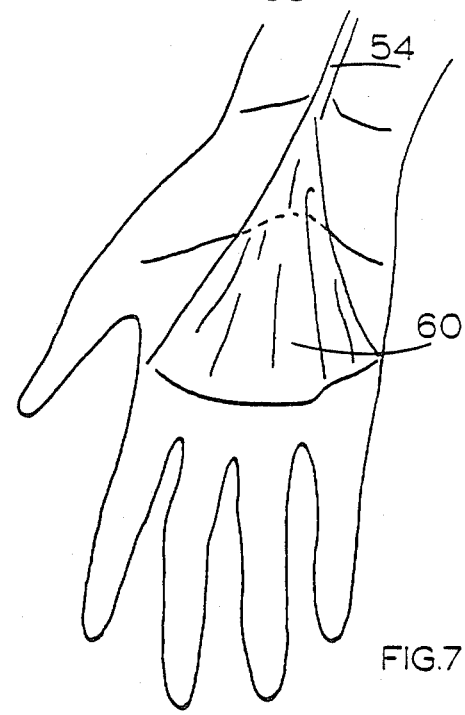
Figure 8:
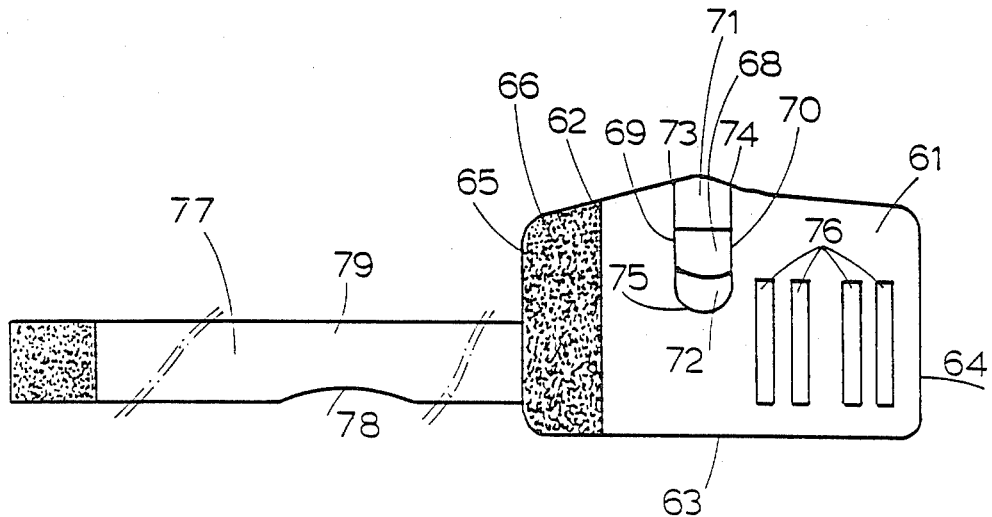
Figure 9:
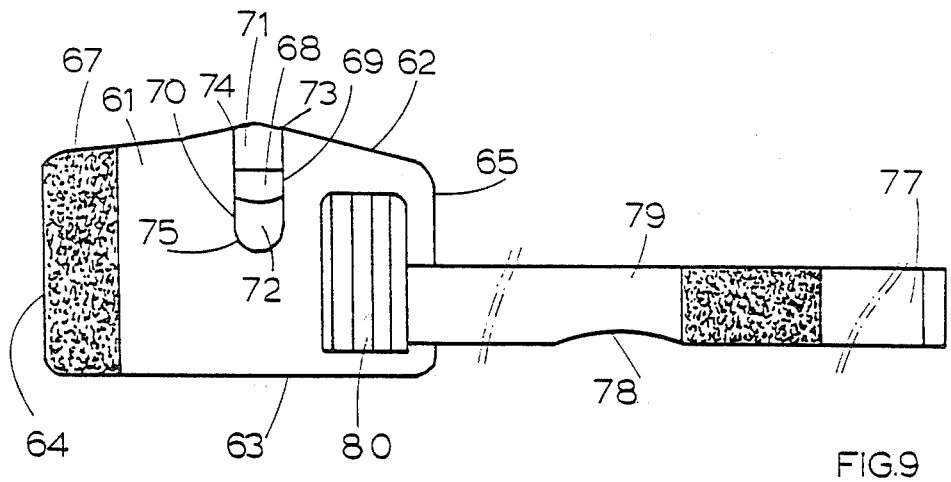

FIG. 1 a diagrammatic representation of the position of a few tendons in the neighbourhood of the left ankle joint;

FIG. 2 a support for a left ankle according to the invention in closed state;

FIG. 3 the support according to FIG. 2, opened along a split;

FIG. 4 a medial side view of the support according to FIG. 2;

FIG. 5 a lateral side view of the support according to FIG. 2;

FIG. 6 a palmar view of the position of a few tendons near a right-hand wrist joint;

FIG. 7 a palmar view of the position of a tendon near a right-hand wrist joint;

FIG. 8 a view of the inside of a support for a right-hand wrist according to the invention, and FIG. 9 a view of the outside of a support according to FIG. 8.

In FIG. 1 is shown a left foot with a part of the leg below the knee 2, which are joined via the tarsus (tarsal joint) 3. From the leg below the knee 2 tendon 4 of the m. extensor digitorum longus (long toe extensor), tendon 5 of the m. peronaeus brevis (short calfbone muscle) and tendon 6 of the m. peronaeus longus (long calfbone muscle) extend over the instep into foot 1. Tendon 4 branches into four sub-tendons 7, 8, 9 and 10 extending into respectively the second toe 11, the third toe 12, the fourth toe 13 and the fifth toe 14. Tendon 4a may be present as the fifth sub-tendon of tendon 4 and be fastened to the metatarsal bone of the fifth toe, but may, however, also run as a tendon of an existing m. peronaeu tetius-from the leg to the foot. Tendon 4 passes under retinaculum m. extensorum superius 15 and retinaculum mm. extensorum inferius 16. Tendons 5 and 6 pass under retinaculum mm. peronaeus superius 17 and the retinaculum mm. peronaeus inferius 18. Tendons 4, 5 and 6 are fixed sideways by the retinacula covering them. Tendons 4, 5 and 6 with their covering retinacula are all of them situated laterally of the sagittal plane between the second toe 11 and the third toe 12 indicated by I. In other words, these tendons are all situated on the left half of the left foot and of the left leg below the knee. It is these tendons which by the contraction of their corresponding muscles impart to the foot a movement which is substantially the result of a dorsiflexion, and an abduction, so respectively of an upward movement and a movement sideways of the foot as indicated by the arrows A and B respectively in FIG. 1. It is the resulting movement opposed to the excessive movement of the foot occuring in most ankle injuries, which is referred to as spraining. So this last-mentioned movement is substantially the result of a plantar flexion and an adduction of the foot as indicated by, respectively, arrows C and D in FIG. 1. In the vast majority of cases the spraining results in excessive stretching or tearing of the ligamentum talofibulare anterius, a ligament connecting the talus (ankle bone) with the fibula (calfbone). In order to protect this ligament against excessive stretching, certainly when this ligament is weak by nature, the support according to FIGS. 2-5 is applied. To enhance the favourable effect of this support, the propriocetive sensibility is utilized also. The fact is that when the tendons mentioned above are stimulated by pressure on or by massage of the skin over these tendons, the muscles of the corresponding tendons will contract and will relieve weak ligament by the initiation of the resulting movement of the dorsiflexion and the abduction of the foot. This pressure or massage is now brought about by applying a strip of chamois leather on the inside of a support drawn in FIG. 2, intended for the left ankle, substantially consisting of a bent sleeve 19 with a straight leg portion 20, a bent heel portion and a straight foot portion 2. The straight leg portion 20 terminates in an edge of the leg portion 23 and the straight foot portion 22 terminates in an edge of the foot portion 24. On the concave side 25 of the bent sleeve 19 there is a strip 26 consisting of a material more elastic than the rest of sleeve 19, which consists of elastic material. This strip 26, extending between the edge of the leg portion 25 and the edge of the foot portion 24, serves to make the support suitable for a few foot sizes. On the inner surface 27 of the support in a lateral position in respect of the plane indicated by II, a part of the surface 28 between the edge of leg portion 23 and the edge of foot portion 24 has been provided with chamois leather having a higher coefficient of friction in respect of the skin than the rest of the material of the support. This strip of chamois leather is indicated by dotted lines 29 and 30. Now, when the support of FIG. 2 is applied round the foot of FIG. 1 with plane II coinciding with plane I, the strip of chamois leather 28 lies against the part of the skin surface covering tendons 4, 4a, 5, 6, 7, 8, 9 and 10. Already with a light movement of the foot, this part of the skin is taken along by the chamois leather and the proprioceptively sensible receptors in the tendinous tissue, which are not deep under the skin, are stimulated.

The application of the support round the foot is facilitated by the presence of a split 31 from the edge of the leg portion 23 to a place 32 near the edge of the foot portion, along which the support can be opened as indicated in FIG. 3. Thus a wide instep is created eliminating to a large extent the very difficult sliding over the skin. After the support has been put on, edges 33 and 34 of the split can be closed with a zip 35.

The support drawn in FIG. 2 has a busk 36 applied crosswise under the foot before heel 37. On the medial side of the support the position of the busk is the same as visible on the lateral side in FIG. 2, where the busk is bent along a line vertically upwards 38, virtually horizontally 39 to beyond malleolus lateralis 40 and vertically upwards 41 to the edge of leg portion 23. Using stitchings 42 drawn in FIGS. 4 and 5 this busk is confined against the outside of the support.

As drawn in FIGS. 4 and 5, the support has short bandages 43 and 44, the lateral cross bandage and the medial cross bandage respectively, fastened under the foot portion. Bandage 43 is intended to be fastened as a lateral bandage along the lateral side of the support, crosswise over instep 45, medially at 46 on the proximal side of the support. Bandage 44 is intended to be fastened as a medial bandage along the medial side of the support, crosswise over instep 45, laterally at 47 on the proximal side of the support. They oppose a plantar flexion of the foot and set limits to the abduction and the adduction, that is the lateral and medial rotation of the foot. Morever, the two bandages increase the pressure at places where chamois leather is applied to the inner surface of the support.

The long bandages 48 and 49 fastened also under the foot portion serve to apply more pressure on and/or more support to the foot. They have a function independent of that of the short bandages.

FIG. 6 shows the position of the muscular tendons extending, right under the palmar skin of forearm and hand, from the forearm over the carpus 50 (wrist joint) into the hand, which tendons can cooperate in effecting a palmar flexion of the hand. 51 indicates the tendon of the m. flexor carpi ulnaris, 52 the four sub-tendons of the m. flexor digitorum superficialis and 53 the tendon of the m. flexor carpi radialis. In FIG. 7 tendon 54 of the m. palmaris longus has been drawn, which is even closer to the surface. Tendon 51 extends via the pisiform bone and the hamate bone to the metacarpal bone of the fifth finger (little finger). The four sub-tendons 52 reach up to the middle phalanges of the second finger 56, the third finger 57, the fourth finger 58 and the fifth finger 55. Tendon 53 reaches as far as the metacarpal bone of the second finger 56, sometimes also as far as that of the third finger 57. Tendons 52 and 53 pass through the canalis carpi (not drawn), these are ducts formed by the m. retinaculum flexorum 59 and carpal bones. Tendon 51 is situated closer towards the ulnar side of the wrist and the hand. Tendon 54 in FIG. 7 branches out into the palmar aponeurosis 60, a tissue consisting of many longitudinal and cross fibres and fastened in many ways to metacarpal parts, inter alia with the longitudinal fibres to the flexor tendons of the 2nd-5th fingers.

The muscles described can be innervated proprioceptively in the neighbourhood of the wrist joint, on the palmar and ulnar sides thereof, to initiate a palmar flexion of the hand. A support suitable for that purpose is illustrated with its inside in FIG. 8 and with its outside in FIG. 9. This wrist support substantially consists of a rectangular wrapper 61 with a distal side 62 of the rectangle, a proximal side 63 of the rectangle parallel thereto, a palmar side 64 of the rectangle and a dorsal side 65 of the rectangle parallel thereto. Using fasteners, for instance hook and pile tapes 66, 67, the wrapper can be shaped to form a sleeve. After the application of the wrist support for the right-hand wrist as shown in the drawing, the palmar and dorsal sides of the rectangle are on the ulnar side of the wrist and the hand. Between the palmar side 64 of the rectangle and the dorsal side 65 of the rectangle there is a U-shaped recess 68 having its mouth on the distal side 62 of the rectangle. Between legs 69 and 70 of the U, the recess is bridged by two elastic strips of material 71 and 72, which have a greater elasticity than the material of wrapper 61, and of which strip 72 has been applied in excess for bridging the distance. The first strip 71 extends from the ends 73 and 74 of the legs of the U and the second strip 72 extends from the closed end 75 of the U. In the application of the support, the thumb can be inserted between strips 71 and 72 and is thus comfortably supported at its base.

By far the larger part of the wrist joint injuries consists in an excessive dorsal flexion, so bending backwards of the hand, in consequence of which one or more ligaments connecting, on the palmar side of the wrist joint, the carpal bones with each other and the carpal bones with the ulna and with the radius are stretched too far. The support described is suited for applying the invention. By applying pieces of chamois leather 76, see FIG. 8, on the inner surface of the support it is exactly those parts of the skin that are covered after the application under which tendons 51, 52, 53 and 54 are situated. The muscles of these tendons are proprioceptively innervated to initiate a palmar flexion when the chamois leather surface portions move the skin to and fro during the movements of the hand. In order to provide support to the thumb the support is provided with an elastic bandage 77 fastened to the dorsal side 65 of the rectangle, which bandage is long enough to cover the way from the ulnar side of the wrist: palmar, radial, dorsal sides of the forearm, ulnar and palmar sides of the hand, between the thumb and forefinger obliquely over the dorsal side of the hand, over ulnar, palmar and radial sides of the forearm and then obliquely to the dorsal side of the hand. On its proximal side the bandage has a recess 78 so that a narrowing 79 exists, which finds its position between thumb and forefinger after the application of the support. The bandage described enhances the action of the support, because it excercises pressure on the chamois leather surface portions. Stitchings 80 may serve to incorporate busks.

Also without chamois leather in parts of the surface, the described wrist support offers advantages. It can be applied easily, it provides a comfortable support for the base of the thumb and, with the narrowing of the bandage, the bandage firmly presses the muscular tissue of the caput transversum fastened to the tendon of the m. adductor pollicis so that an adduction and opposition of the thumb is brought about, which means that the thumb is pushed away from those positions in which most injuries occur.

The fastening of the bandages of the supports described can be realized as known in the art. Preference is given to fastening with hook and pile tape.

I claim:

1. A support for a part of the body including a joint, comprising:
   a sleeve member made substantially from elastic material and extending, after its application, between a proximal line and a distal line in respect of the joint,
   at least one frictional portion defined on the inner surface of the sleeve member, said frictional portion having a greater coefficient of friction in respect of the skin than the coefficient of friction of the other portions of the inner surface of the sleeve member, said frictional portion being defined on a portion of the inner surface of the sleeve member that is adapted to be in contact, after the application of the support to the part of the body, with portions of the surface of the skin having at least one of muscular and tendonous tissue underneath which can be innervated proprioceptively so as to initiate a predetermined change in position between skeletal parts situated on either side of the joint when the part of the body is moved and said frictional portion inhibits the movement of skin in contact therewith.

2. A support according to claim 1, wherein said frictional portion consists of chamois leather.

3. A support according to claim 1, wherein said frictional portion is discontinuous.

4. A support according to claim 1, wherein the support if for an ankle joint and said frictional portion is situated in a strip of the support between the proximal and distal limits, which strip is in contact, after the application of the support, with a strip of the skin situated laterally in respect of a sagittal plane between the 2nd and 3rd toe.

5. A support suitable as a support for an ankle joint according to claim 4, wherein the support includes a first elastic material substantially consisting of a sleeve which is bent in the shape of a foot and open at both ends, comprising a straight leg portion terminating in an edge of the leg portion, a bent heel portion linking up with the leg portion and a straight foot porion linking up with the heel portion and terminating in an edge of the foot portion, the concave side of the sleeve including a strip extending between the edge of the leg portion and the edge of the foot portion which consists of a second elastic material having a greater elasticity than the first elastic material and in that on the concave side, between the first and the second elastic material, a split has been provided from the edge of the leg portion to near the edge of the foot portion, which split can be closed with fasteners.

6. A support according to claim 5, wherein the support has two crossed bandages fastened to the sole of the foot portion of the support, before the heel portion, both having a length sufficient for one to be fastened medially along the foot portion, cross-wise over the instep and laterally on the parts inside the support, and for the other to be fastened laterally along the foot portion, crosswise over the instep medially on the proximal side of the support.

7. A support according to claim 5, wherein the support is provided with a busk passing crosswise under the foot before the heel and subsequently bent medially and laterally along the line: vertically upwards, virtually horizontally to beyond the malleoli and vertically upwards to the edge of the leg portion of the support.

8. A support for a wrist joint according to claim 1, wherein said frictional portion is disposed in an area extending from the proximal side of the support, which area is in contact, after the application of the support, with the palmer and ulner parts of the skin of the forearm and the hand.

9. A support suitable as a support for a wrist joint according to claim 8, wherein the support is a substantially rectangular wrapper with a distal side of the rectangle and a proximal side of the rectangle parallel to it, a palmar side of the rectangle and a dorsal side of the rectangle parallel to it, which wrapper can be shaped to form a sleeve by means of fasteners along the palmar and dorsal sides of the retangle, in that there is a U-shaped recess between the palmar and dorsal sides of the rectangle having its mouth on the distal side of the rectangle, which recess is bridged, between the legs of the U, by two elastic strips of material having a greater elasticity than the material of the wrapper, the first of which extends from the ends of the legs on the U and the second from the closed end of the U in such a manner that a thumb can be inserted between the bridging strips, in that an elastic bandage is present fastened to the dorsal side of the rectangle and having sufficient length to cover the way: palmar, radial, dorsal sides of the forearm, ulnar and palmar sides of the hand, between thumb and forefinger obliquely over the dorsal side of the hand, over ulnar, palmar and radial sides of the forearm and then obliquely to the dorsal side of the hand, and in that the bandage is provided on its proximal side with a recess for the portion applied between thumb and forefinger.

10. A support according to claim 9, wherein at least the strip extending from the closed end of the U has an excess of material.

11. A support according to claim 1, further comprising bandage means fastened to said sleeve member so as to provide at least one of greater pressure on and more support to the part of the body to which the sleeve member is mounted.

* * * * *